(12) United States Patent
Horstmann

(10) Patent No.: US 7,858,113 B2
(45) Date of Patent: Dec. 28, 2010

(54) METHOD AND DEVICE FOR IMPROVING THE PERMEABILITY OF THE HUMAN SKIN

(75) Inventor: Michael Horstmann, Neuwied (DE)

(73) Assignee: LTS Lohmann Therapie-Systeme AG (DE)

( * ) Notice: Subject to any disclaimer, the term of this patent is extended or adjusted under 35 U.S.C. 154(b) by 1343 days.

(21) Appl. No.: 10/566,236

(22) PCT Filed: Jul. 20, 2004

(86) PCT No.: PCT/EP2004/008068

§ 371 (c)(1),
(2), (4) Date: Jan. 27, 2006

(87) PCT Pub. No.: WO2005/011797

PCT Pub. Date: Feb. 10, 2005

(65) Prior Publication Data

US 2007/0020323 A1    Jan. 25, 2007

(30) Foreign Application Priority Data

Aug. 1, 2003   (DE) ............................... 103 35 231

(51) Int. Cl.
*A61L 15/16* (2006.01)
*A61F 13/02* (2006.01)
(52) U.S. Cl. ...................... 424/449; 424/447
(58) Field of Classification Search ................. 424/449
See application file for complete search history.

(56) References Cited

U.S. PATENT DOCUMENTS 5,616,140 A    4/1997   Prescott 6,315,772 B1    11/2001   Marchittto et al.

FOREIGN PATENT DOCUMENTS

| DE | 296 12 198 U1 | 10/1996 |
| DE | 195 44 255 A1 | 3/1997 |
| DE | 695 26 371 T2 | 11/2002 |
| DE | 101 28 629 A1 | 12/2002 |
| EP | 0 294 122 A1 | 12/1988 |
| EP | 0 841 965 B1 | 4/2002 |
| WO | WO 98/58685 | * 12/1998 |

* cited by examiner

*Primary Examiner*—Jake M. Vu
(74) *Attorney, Agent, or Firm*—Frommer Lawrence & Haug LLP

(57) ABSTRACT

The invention relates to a method for improving the permeability of the human skin in order to transdermally supply active substances, permeability being improved by means of a plaster that is transparent in at least some areas, contains active substance, and is flexible in at least some areas, and at least one external light source. According to said method, light that is emitted at least for a short period of time by an external light source and normally impinges at least some areas of the plaster is focused onto the stratum corneum of the skin with the aid of a plurality of individual focusing lenses which are integrated into the plaster so as to bring about changes in the stratum corneum, said changes improving the permeability of the skin. The inventive method for improving the permeability of the human skin allows for reproducible permeability for specific active substances.

10 Claims, 2 Drawing Sheets

METHOD AND DEVICE FOR IMPROVING THE PERMEABILITY OF THE HUMAN SKIN

The invention relates to a method for improving the permeability of the human skin for transdermal delivery of active substances, by means of a plaster which is transparent in at least some areas, contains active substance, and is flexible in at least some areas, and by means of at least one external light source.

Transdermal therapeutic systems have been in established use for years in the treatment of various topical and systemic diseases. Active substances such as nicotine, estradiol, nitroglycerin, and fentanyl, for example, can in this way be administered in a more targeted manner than is possible when they are taken orally, because of the much improved pharmacokinetics and avoidance of the first-pass effect. However, the choice of active substances suitable for transdermal delivery is limited. Although transport is possible in the case of some active substances, the formulations nevertheless require an impracticably large surface area.

One possible solution to the problem lies in permeation enhancers. These enhancers, for example ethanol, butanol, and other short-chain alcohols, are chemical substances which are added to the formulation in order to temporarily increase the permeability of the human skin. A sufficiently high flow rate of the pharmaceutical active substance is thereby permitted. However, these enhancers are taken up by the body and place a burden on the metabolic processes of the body.

Therefore, the present invention is based on the object of developing a method for improving the permeability of the human skin, which method, without causing systemic effects, permits a reproducible permeability for certain active substances.

This object is achieved by the features of the main claim and independent claim 3. Light emitted at least briefly from an external light source and impinging normally with respect to the plaster, in at least some areas, is focussed through a multiplicity of individual positive lenses, integrated in the plaster, onto the stratum corneum of the skin, in order in this way to generate stratum corneum changes which improve the permeability of the skin.

For this purpose, the plaster comprises at least one top layer and at least one active-substance-containing self-adhesive layer. The top layer and the active-substance-containing layer are transparent in at least some areas, the transparent areas lying over one another inside the plaster, and the top layer comprising a multiplicity of optical positive lenses organized in a planar arrangement.

The transdermal therapeutic system thus comprises, inter alia, at least one active-substance-containing matrix layer directed toward the skin, and a transparent, geometrically contoured top layer. The system is affixed temporarily to the skin in the form of a plaster. Such an arrangement permits the use of light sources for improving the transdermal absorption during the period when the plaster is being worn.

Further details of the invention are set forth in the dependent claims and in the following description of schematically illustrated embodiments.

BRIEF DESCRIPTION OF THE DRAWINGS

FIG. 1 illustrates a physical method by which the transdermal delivery of active substance is greatly accelerated. For this purpose, for example, a self-adhesive plaster (10) is used which has a transparent top layer or backing layer (12, 13) and at least one active-substance-containing and likewise transparent adhesive layer or matrix layer (50, 40). The top layer (12) comprises an array of optical lenses (20-22). The plaster (10) affixed to the skin (6) is illuminated at least briefly by a light source (1) having a high intensity of illumination. The light (2) impinging at least almost normally with respect to the rear face (14) of the plaster is separately focused by the individual positive lenses (20-23) and projected onto the stratum corneum (7) of the skin (6). At the individual focal points or focal lines, small focal spots (8) are created which keep the stratum corneum (7) thin and open for transport of active substance. The focal lines arise because of the diacaustic of the positive lenses.

Figure 1:
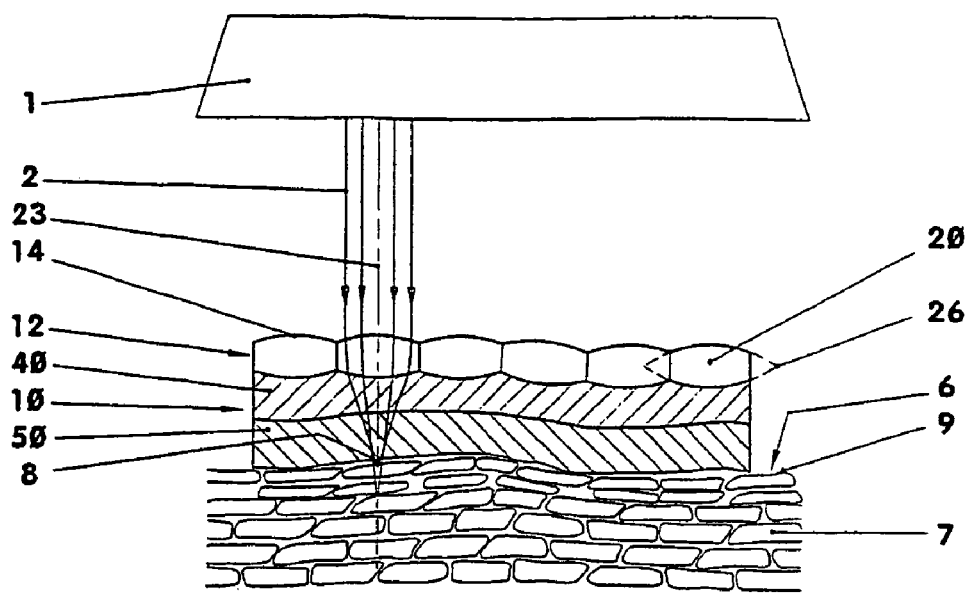
FIG. 1 shows a plaster and stratum corneum in cross section.

The matrix layer and/or adhesive layer (40, 50) here constitute an active substance depot which is able to release its active substance over hours or days, for example.

The plaster (10) stored prior to use is protected from unwanted release of active substance, or from loss of active substance, by at least a protective film adhering to the adhesive layer (50).

The top layer (12) is in this case a transparent film, for example, in which a large number of small lenses (20) are integrated. Each individual lens (20) has, for example, a double convex shape, of which the centers of curvature each lie on an optical axis (23). The individual optical axes (23) are generally oriented normally with respect to the particular surface element of the rear face (14) of the plaster. The distance between the optical axes (23) of two adjacent lenses (20) is 50 to 500 µm, for example. In certain cases, the respective distance can be increased to one millimeter. The focal length of the individual lenses (20) is dimensioned, taking account of the possibly different indices of refraction of the lens material and of the matrix materials, such that the mean focal length of ca. 10 to 20 µm lies under the outer face (9) of the skin (6) in the stratum corneum (7). For example, with a top layer (12) having a thickness of 40 µm and a matrix and adhesive layer (40, 50) having a thickness of 100 µm, the mean focal length is thus 135 µm.

Figure 2:
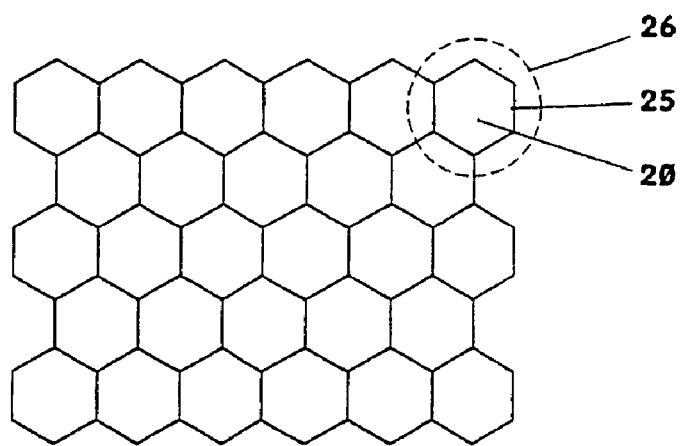
FIG. 2 shows a partial top view of a lens array without the plaster edge.

Radially, the lenses (20) according to FIG. 2 are delimited, for example, by the perimeter face (25) of a straight, regular and hexagonal prism. A complete lens (20) would have the circular outer contour (26) shown in FIGS. 1 and 2. Alternatively, the lenses (20) can also each have a cylindrical outer contour. The resulting interstices would then be filled by plane surfaces, for example. The mean thickness of the flexible film (12) containing the lenses (20) is ca. 40-100 µm. The total surface area of the transparent part of the plaster (10) is, for example, between 2 and 50 $cm^2$, depending on the application in question.

In applications in which the illumination results in a visible partial tinting of the stratum corneum, the lenses in the outer plaster areas can, for example, be made partially opaque or can be made without a convex curvature in order to reduce the transition contrast from untinted to tinted stratum corneum, for example for cosmetic reasons.

This principle can of course also be reversed. Thus, a tanned pattern in the form of a temporary tattoo can be produced on the stratum corneum by means of a specific arrangement of lenses, generating focal points, and of optically inactive interstices.

Possible materials for the top layer are: polycarbonate, polyethylene, polymethyl methacrylate, polyethylene terephthalate and other polyesters, polypropylene, acrylate polymers, polyamides, and inorganic glasses or the like, provided these materials have optically refractive and transparent properties.

Since high demands are not generally placed on the optical quality of the lens arrays, the film (12) can, for example, be produced by injection molding. In the case of micro-lens arrays with smaller than average lenses, the film (12) can also be produced by microlithography.

Figure 3:
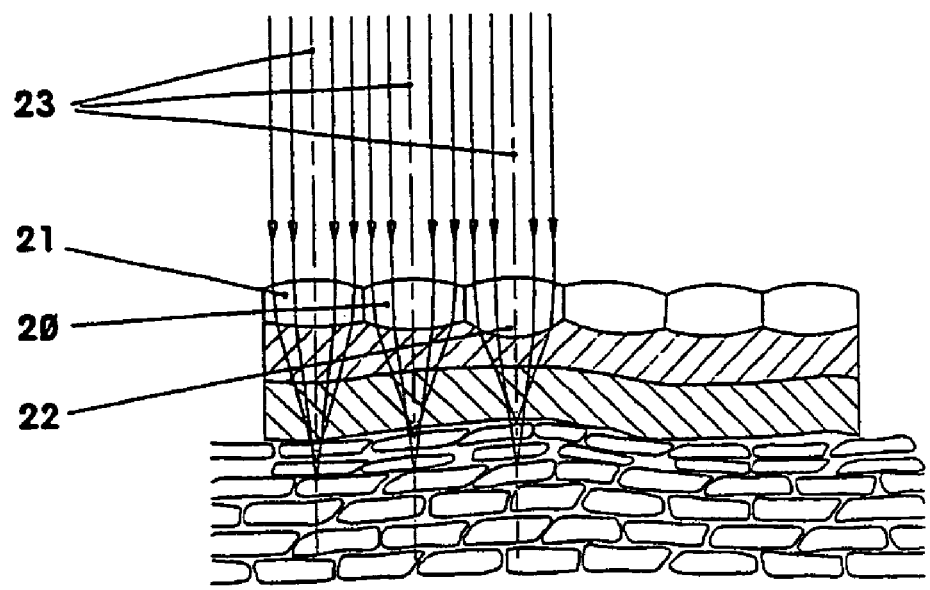
FIG. 3 shows the same as FIG. 1, but with lenses of different focal lengths.

According to FIG. 3, lenses (20-22) of different focal lengths can be arranged in a lens array. In the illustrative embodiment, three different lenses (20, 21, 22) are used which are arranged, for example, in a uniform distribution within the lens array. Their focal lengths vary in a range of from 10 to 50 μm, for example. With the aid of such a lens array, a thicker stratum corneum can temporarily be made more permeable.

Figure 4:
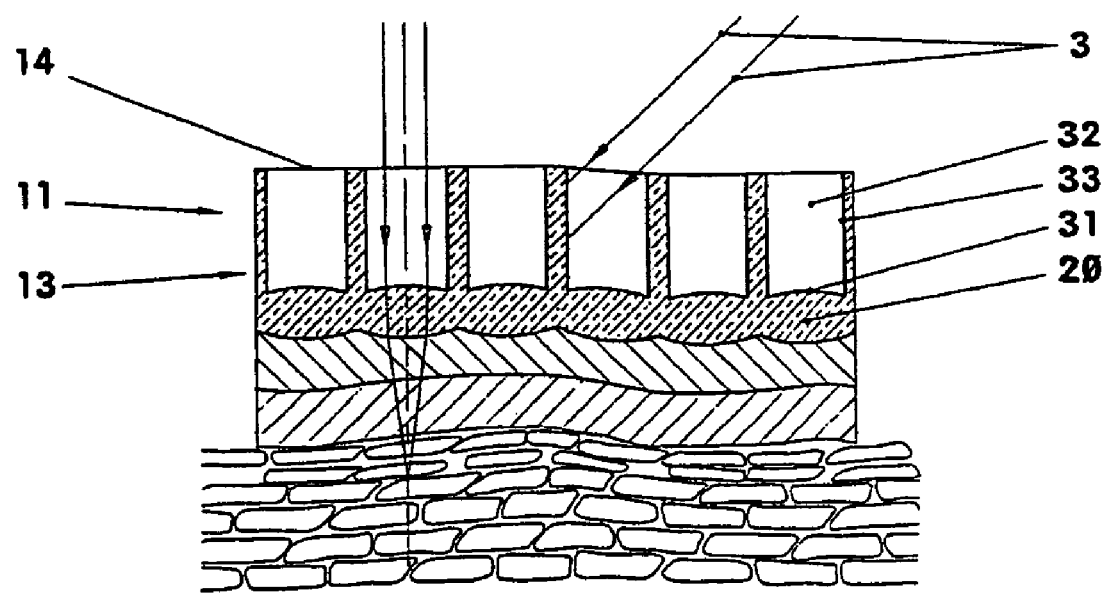
FIG. 4 shows the same as FIG. 1, but with mechanical extraneous light shading.

In FIG. 4, a plaster is shown whose top layer (13) corresponds for example to three to four times the thickness of the material of the top layer (12) from FIG. 1. Here, the rear convex surfaces (31) of the individual lenses (20) each form the bottom of a blind hole (32) that has been let into the top layer (13) The inner surfaces (33) of the blind holes (32), except for lens surface (31), have, for example, a coating either prohibiting total reflection or permitting the latter only in the form of diffuse reflection. If appropriate, the coating is in the form of a matt black color. Light (3) impinging at an oblique angle into the blind holes (32) is then able to cause virtually no change in the skin beneath the lens.

Instead of the lens array provided with blind holes (32), it is also possible to use a lens array known from FIG. 1 onto which a flexible honeycomb grid is affixed. The honeycomb grid, which is made for example from a material other than that of the lens array, comprises, for example, a multiplicity of tubes of hexagonal cross section. The center lines of the tubes are oriented substantially normal with respect to the skin surface.

Another variant for stopping extraneous light is to arrange one or more stubs on almost every individual edge of the individual lenses (20-22), said stubs being arranged substantially normal with respect to the skin surface (9). The stubs protruding from the outer face (14) of the plaster cast a shadow across the individual lens surfaces (31) in the case of extraneous light.

Another alternative for controlling the amount of light to be applied to the skin lies in the use of phototrophic glasses. Lens materials of this kind reversibly darken the lenses within the space of seconds to minutes. Complete coverage of the lens array by means of an opaque self-adhesive covering film is also conceivable.

Instead of this kind of multiple dimming, it is also possible to use lens materials which become permanently opaque or turn dark after minutes or hours, as a result of ageing caused by the action of light.

With a defined illumination of the corresponding area of the stratum corneum supporting the plaster, the transport of active substance through the skin can be controlled in a reproducible manner. Important influencing factors here are, for example, a constant level of irradiation and a constant distance between the light source and the plaster. Since a single delivery of light energy or radiant energy at the start of treatment is in some cases insufficient, it may be necessary to configure a flash lamp which emits light impulses at defined time intervals, for example minutes or hours, to ensure that the skin structures created by the focal lens action are kept open.

LIST OF REFERENCE NUMBERS 1 light source
2 light, direction of light normal with respect to plaster surface
3 light, direction of light oblique with respect to plaster surface
6 human skin
7 stratum corneum
8 focal spots, changes in stratum corneum
9 surface of the skin
10 plaster
11 plaster with partially shaded lenses
12, 13 top layer, backing layer, film
13 top layer with blind holes
14 outer face of plaster, rear face of plaster
20-22 lenses, convex lenses
23 optical axis
25 perimeter surface
26 outer contour
31 surfaces, curved
32 blind holes
33 inner face, cylindrical
40 matrix layer
50 adhesive layer

The invention claimed is:

1. A method for improving the permeability of the human skin (6) for transdermal delivery of active substances, by means of a plaster (10, 11) which is transparent in at least some areas, contains active substance, and is flexible in at least some areas, and by means of an external light source (1), the plaster (10, 11) comprising at least one active-substance-releasing layer (40) and at least one top layer (12, 13) which contains a multiplicity of optical positive lenses (20-22) organized in a planar arrangement, through which a multiplicity of individual changes in stratum corneum (8) improves the permeability of the skin (6) are generated in the stratum corneum (7) of said skin (6) with the aid of light (2) at least impinging on the top layer (12, 13) from at least one light source (1).

2. The method as claimed in claim 1, characterized in that the changes (8) in the stratum corneum each lie in the focal points or focal lines of the positive lenses (20-22).

3. A plaster for transdermal delivery of active substances, with at least one top layer and at least one self-adhesive layer that contains active substance, characterized in that the top layer (12, 13) and the layer (40) containing active substance are transparent in at least some areas,
the transparent areas lying over one another inside the plaster (10, 11),
the top layer (12, 13) comprises a multiplicity of optical lenses (20-22) organized in a planar arrangement, and
the focal points of the optical lenses (20-22) lie in the stratum corneum (7) of the skin (6) supporting the plaster.

4. The plaster as claimed in claim 3, characterized in that the layer (40) is an adhesive layer,
or
in that the layer (40), as an exclusively active-substance-containing layer, is provided with an adhesive layer (50) which is permeable to active substance and oriented toward the skin (6).

5. The plaster as claimed in claim 3, characterized in that at least some of the optical lenses (20-22) have different focal lengths.

6. The plaster as claimed in claim 3, characterized in that, on that side of the plaster (11) directed away from the human skin (6), one or more individual edge of the individual optical lenses (20-22) are arranged normal with respect to the skin surface (9).

7. The plaster as claimed in claim 3, wherein each optical lens (20-22) have a double convex shape wherein the centers of curvature lie on an optical axis (23).

8. The plaster as claimed in claim 7, wherein the distance between the optical axes (23) of two adjacent optical lenses (20-22) is 50 to 500 µm.

9. The plaster as claimed in claim 8, wherein radially, the optical lenses (20-22) are delimited by a perimeter face (25) of a straight hexagonal prism.

10. The plaster as claimed in claim 9, wherein the optical lenses (20-22) are polymers and inorganic glasses having optically refractive and transparent properties.

* * * * *